US007807427B2

(12) United States Patent
Koshland, Jr.

(10) Patent No.: US 7,807,427 B2
(45) Date of Patent: Oct. 5, 2010

(54) METHODS AND COMPOSITIONS FOR PRODUCTION OF METHANE GAS

(75) Inventor: Daniel E. Koshland, Jr., Lafayette, CA (US)

(73) Assignee: The Regents of the University of California, Oakland, CA (US)

( * ) Notice: Subject to any disclaimer, the term of this patent is extended or adjusted under 35 U.S.C. 154(b) by 510 days.

(21) Appl. No.: 11/587,777

(22) PCT Filed: Sep. 15, 2006

(86) PCT No.: PCT/US2006/036196

§ 371 (c)(1),
(2), (4) Date: Oct. 27, 2006

(87) PCT Pub. No.: WO2007/035579

PCT Pub. Date: Mar. 29, 2007

(65) Prior Publication Data

US 2009/0035832 A1 Feb. 5, 2009

Related U.S. Application Data

(60) Provisional application No. 60/717,791, filed on Sep. 15, 2005.

(51) Int. Cl.
  *C12P 5/00* (2006.01)
  *C12P 5/02* (2006.01)
  *C12N 1/20* (2006.01)
  *C12M 1/00* (2006.01)
  *C12M 3/00* (2006.01)

(52) U.S. Cl. .............. 435/166; 435/167; 435/252.3; 435/292.3; 435/294.1; 435/303.2

(58) Field of Classification Search ............ None
See application file for complete search history.

(56) References Cited

U.S. PATENT DOCUMENTS 4,318,993 A   3/1982  Ghosh et al.
5,137,828 A * 8/1992  Robinson et al. ......... 435/292.1
6,699,696 B2 * 3/2004  Woods et al. ............... 435/161

OTHER PUBLICATIONS

Teplyakov et al., Lab-Scale bioreactor integrtaed with active membrane system for hydrogen production: experience and prospects. Int. J. Hydrogen Energy., 2002, vol. 27: 1149-1155.*
Broun et al., Catalytic plasticity of fatty acid modification enzymes underlying chemical diversity of plant lipids. Science, 1998, vol. 282: 1315-1317.*
Devos et al., Practical limits of function prediction: Proteins: Structure, function, and Genetics, 2000, vol. 41: 98-107.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol.,2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*

* cited by examiner

*Primary Examiner*—Ganapathirama Raghu
(74) *Attorney, Agent, or Firm*—Edward J. Baba; Khin K. Chin; Bozicevic, Field & Francis LLP

(57) ABSTRACT

The present invention provides methods and compositions for sustained methane production from atmospheric $CO_2$ and solar energy from the sun. In general the methods involve culturing cyanobacteria in a first culture vessel and collecting and diverting the photosynthesis products, including glucose or acetic acid, to a second culture vessel including methanogenic bacteria. The photosynthesis products are then used as nutrients by the methanogenic bacteria in the second culture vessel in the production of methane. The methane produced is subsequently collected and used as a clean energy source. The invention also features compositions, including genetically modified cyanobacteria and systems for use in the methods of the invention.

10 Claims, 5 Drawing Sheets

SEQUENCE LISTING

<160> NUMBER OF SEQ ID NOS: 14

<210> SEQ ID NO 1
<211> LENGTH: 97
<212> TYPE: DNA
<213> ORGANISM: Artificial Sequence
<220> FEATURE:
<223> OTHER INFORMATION: synthetic oligonucleotide

<400> SEQUENCE: 1
aattccgatc cgcgaaatt aatacgactc actataggga gaccacaacg gtttcccttc    60
agaaataatt ttgtttaact ttaagaagga gatatag                            97

<210> SEQ ID NO 2
<211> LENGTH: 97
<212> TYPE: DNA
<213> ORGANISM: Artificial Sequence
<220> FEATURE:
<223> OTHER INFORMATION: synthetic oligonucleotide

<400> SEQUENCE: 2
gatcctatat ctccttctta aagttaaaca aaattatttc tgaagggaaa ccgttgtggt    60
ctccctatag tgagtcgtat taatttcgcg gatcgg                              97

<210> SEQ ID NO 3
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 3
agcttctagc ataacccctt ggggcctcta acgggtctt gaggggtttt ttgatatca      59

<210> SEQ ID NO 4
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 4
tatgatatca aaaaccccct caagacccgt ttagaggccc caaggggtta tgctaga       57

<210> SEQ ID NO 5
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 5
cgcggatccg cggctgaaag tttcggactc agtag                               35

<210> SEQ ID NO 6
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 6
ggcatgtcga ctctccctag agatatgtca g                                   31

```
<210> SEQ ID NO 7
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 7
ggaggtcgac atgagttata ctgtcggtac c                              31

<210> SEQ ID NO 8
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 8
cgctgcagtt actagaggag cttgttaaca ggc                            33

<210> SEQ ID NO 9
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 9
gaggcatgcg gaggtgctgc catgactgct gtcgttctcc                     40

<210> SEQ ID NO 10
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 10
gctgcatgca ctagagcttg cggaagagg                                 29

<210> SEQ ID NO 11
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 11
cgctctagaa tggttatgaa acaaacaaaa c                              31

<210> SEQ ID NO 12
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 12
gcgctgcagc tattaaaacc caccctgtcc aatttg                         36

<210> SEQ ID NO 13
<211> LENGTH: 45
<212> TYPE: DNA
<213> ORGANISM: Artificial Sequence
<220> FEATURE:
<223> OTHER INFORMATION: synthetic oligonucleotide
```

```
<400> SEQUENCE: 13
gaggcatgcg gaggagcctg ttcagatgct ggatagcagc gatcg                           45

<210> SEQ ID NO 14
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 14
gctgcatgcc tatcaattga aagactgtgg ggatcg                                     36
```

METHODS AND COMPOSITIONS FOR PRODUCTION OF METHANE GAS

CROSS-REFERENCE

This application claims the benefit of U.S. Provisional Application No. 60/717,791 filed Sep. 15, 2005, which application is incorporated herein by reference.

BACKGROUND OF THE INVENTION

Present concerns regarding the long term availability of fossil fuels and the increase of atmospheric carbon dioxide ($CO_2$) have given rise to a societal need for new forms of energy. Most alternative resources are in short supply and/or add further to the global warming problem, e.g., nuclear energy and coal. $H_2$ has certain popularityas it combusts to $H_2O$ but it is difficult to handle, i.e., $H_2$ leaks through containers and is explosive. An alternative is methane ($CH_4$), which is an ultimate product of anaerobic degradation of biological wastes and is a natural gas which can be transported easily in pipelines. Moreover, if made from $CO_2$, use of $CH_4$ as a fuel would not increase the net amount of $CO_2$ in the atmosphere.

SUMMARY OF THE INVENTION

The present invention provides methods and compositions for sustained methane production from atmospheric $CO_2$ and solar energy from the sun. In general the methods involve culturing photosynthetic organism, such as cyanobacteria, in a first culture vessel and collecting and diverting the photosynthesis products, such as glucose or acetic acid, to a second culture vessel including methanogenic bacteria. The photosynthesis products are then used as nutrients by the methanogenic bacteria in the second culture vessel in the production of methane. The methane produced is subsequently collected and used as a clean energy source. The invention also features compositions, including genetically modified cyanobacteria and systems for use in the methods of the invention.

The present invention features a method for production of methane by culturing a photosynthetic organism in a first vessel in the presence of carbon dioxide ($CO_2$) and sunlight and/or visible light, wherein the culturing provides for photosynthetic fixation of $CO_2$ to photosynthetic products, collecting and diverting the photosynthesis product to a second vessel comprising methanogenic bacteria, and culturing said methanogenic bacteria to produce methane. In some embodiments, the photosynthetic organism is a photosynthetic cyanobacteria. In some embodiments, the photosynthesis product is glucose or acetic acid. In further embodiments, the cyanobacteria are genetically modified in order to provide for transport of the photosynthetic products. In some embodiments, the visible light source is natural light. In other embodiments, the visible light source is artificial light. In some embodiments, the $CO_2$ source is atmospheric $CO_2$. In other embodiments, the $CO_2$ source is an artificial source.

Another feature of the present invention provides for a system for production of methane, including a first vessel for culturing a photosynthetic organism in the presence of carbon dioxide ($CO_2$) and visible light, and a second enclosed vessel for culturing methanogenic bacteria, wherein said first vessel is in fluid communication with said second vessel. In some embodiments, the visible light source is natural light. In other embodiments, the visible light source is artificial light. In some embodiments, the $CO_2$ source is atmospheric $CO_2$. In other embodiments, the $CO_2$ source is an artificial source. In some embodiments, the system further includes a first conduit connecting the first vessel and the second vessel. In some embodiments, the system further includes a gas storage container in gaseous communication with the second vessel. In some embodiments, the system further includes a second conduit connecting the second vessel with the gas storage container.

Yet another feature of the present invention provides for a genetically modified cyanobacteria expressing at least a first foreign gene, wherein the genetically modified cyanobacteria is capable of transporting products of photosynthesis across the cyanobacteria's membrane. In some embodiments, the transport is passive transport. In other embodiments, the transport is active transport. In some embodiments, the first foreign gene encodes a glucose transporter. In further embodiments, the glucose transporter is Glut-1, which helps genetically modified cyanobacteria to transport photosynthesis products, such as glucose, across the bacterial membranes into the outer solution. In some embodiments this will involve passive transport, i.e. the native bacterial facilitative transporters such as the native glucose transporters which normally let glucose in, or the mammalian transporters such as Glut-1, Glut-2, etc. which let glucose out. In other embodiments this will involve active transporters. In the present case, the foreign gene of a glucose transporter such as glucose-6-phosphatase attached to the native promoter would be used while the native transporter would be deleted.

In certain embodiments, the genetically modified cyanobacteria expresses a second foreign gene. In some embodiments a DNA construct is added to the bacterium and integrated into the chromosome. The DNA construct carries two genes, one is a pyruvate decarboxylase and the other is an aldehyde dehydrogenase. In other the embodiments, first gene is a pyruvate oxidase and the second is an acetate CoA kinase. The purpose is to produce acetic acid as a nutrient for the methanobacteria. In other embodiments, the first foreign gene encodes pyruvate decarboxylase and the second foreign gene encodes aldehyde dehydrogenase. In other embodiments, the first foreign gene encodes pyruvate oxidase and the second foreign gene encodes acetate kinase.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

Included in the drawings are the following figures.

DEFINITIONS

Figure 1:
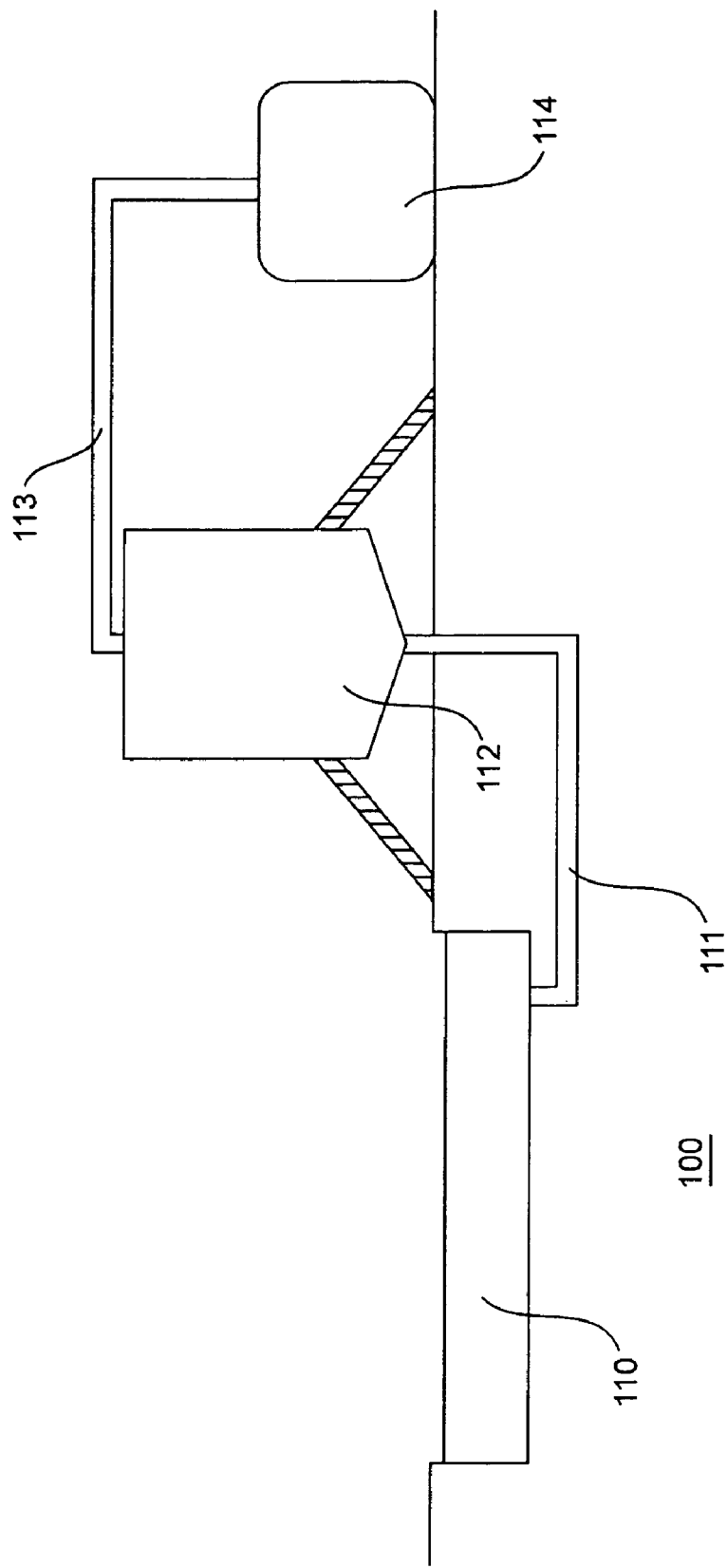
FIG. 1 is a schematic overview of an exemplary system (100) for sustained methane production. The exemplary system includes a first culture vessel (110) for cyanobacteria, a first conduit (111), a second culture vessel (112) for methanogenic bacteria, a second conduit (113), and a storage vessel (114) for methane gas.

As used herein, the terms "methanobacteria", or "methanogenic bacteria" refer to a class of strictly anaerobic prokaryotes that are members of the phylum Euryacheota. These organisms include, for example, the genera *Methanococcus, Methanobacterium, Methanosarcina*. Exemplary methanobacteria are further described in James G. Ferry, Methanogenesis (1993) (Chapman and Hall, New York, N.Y.).

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host. Definitions are based on the conventional nomenclature as described in texts such as Watson, Tooze, et al. The term "DNA construct" will be used to mean a section of DNA carrying one or more genes, promoters, regulatory elements, etc. furthermore, the term "plasmid" refers to a circular DNA construct containing an origin of replication.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

"Gene" refers to a nucleic acid that expresses a specific protein, including regulatory sequences preceding (5' non-coding sequences) and following (3' non-coding sequences) the coding sequence. "Native gene" refers to a gene as found in nature with its own regulatory sequences as in the organism in which it occurs naturally. A "foreign" gene refers to a gene not normally found in the host organism, but that is introduced into the host organism by gene transfer. Foreign genes can comprise native genes inserted into a different organism, or chimeric genes.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Recombinant" as used herein to describe a nucleic acid molecule refers to a polynucleotide of genomic, cDNA, mammalian, bacterial, viral, semisynthetic, synthetic or other origin which, by virtue of its origin, manipulation, or both is not associated with all or a portion of the polynucleotide with which it is associated in nature. The term "recombinant" as used with respect to a protein or polypeptide means a polypeptide produced by expression of a recombinant polynucleotide.

The term "expression", as used herein, refers to the transcription and stable accumulation of sense (mRNA) or antisense RNA derived from the nucleic acid fragment. Expression may also refer to translation of mRNA into a polypeptide.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the compound" includes reference to one or more compounds and equivalents thereof known to those skilled in the art, and so forth.

Standard recombinant DNA and molecular cloning techniques used here are well known in the art and are described by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., Experiments with Gene Fusions, Cold Spring Harbor Laboratory Cold Press Spring Harbor, N.Y. (1984); and by Ausubel, F. M. et al., Current Protocols in Molecular Biology, published by Greene Publishing Assoc. and Wiley-Interscience (1987); and Watson et al., Recombinant DNA: A short course, published by Scientific American (1983).

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods and compositions for sustained methane production from atmospheric CO2 and solar energy from the sun. In general the methods involve culturing photosynthetic organisms, such as genetically modified cyanobacteria, in a first culture vessel and collecting and diverting the photosynthesis products, including glucose or acetic acid, to a second culture vessel containing methanogenic bacteria. The photosynthesis products are then used as nutrients by the methanogenic bacteria in the second culture vessel in the production of methane. The methane produced is subsequently collected and used as a clean energy source or as a hydrocarbon for synthesis of other hydrocarbon products. The invention also features compositions, including genetically modified cyanobacteria and systems for use in the methods of the invention.

The present invention is directed to the use of solar energy to convert carbon dioxide ($CO_2$) to methane ($CH_4$) using biological organisms. In general, the present invention includes a two-step process for generating methane. The first step is converting $CO_2$ present in the atmosphere to photosynthesis products including, for example, glucose, acetic acid, or acetate. The second step is converting the photosynthesis products generated in the first-step to methane. The methane generated by the two-step system is collected and stored for use as energy source, such as in heating, transportation, and other commercial applications The compositions and methods of the invention will now be described in more detail.

Cyanobacteria

Cyanobacteria are photosynthetic bacteria which require light, inorganic elements, nitrogen sources, water and a carbon source, generally $CO_2$, to metabolize and grow. Cyanobacteria are photosynthetic prokaryotes which carry out oxygenic photosynthesis. The main product of the metabolic pathway of Cyanobacteria during aerobic conditions is oxygen and carbohydrates. Exemplary suitable cyanobacteria include those found in Donald Bryant, The Molecular Biology of Cyanobacteria, published by Kluwer Academic Publishers (1994). Representative examples include *Synechococcus* such as *Synechococcus lividus* and *Synechococcus elongatus*; and *Synechocystis* such as *Synechocystis minervae*, such as *Synchocystis* Sp PCC 6803.

In this invention the pyruvate formed in photosynthesis is decarboxylated and converted to acetic acid in one embodiment by inserting two foreign genes into the cyanobacteria (a) a pyruvate decarboxylase and (b) an aldehyde dehydrogenase. In another embodiment it would be a combination of (a) pyruvate oxidase and (b) an acetyl CoA kinase. Both genes in each case would be equipped with powerful native promoters, i.e. cyanobacterial promoters in the growth in cyanobacteria.

The selection of nutrients and other conditions for growing cyanobacteria may be readily made by one of skill in the art with resort to existing knowledge, and depend on a variety of factors, such as the microorganism used, the size and type of the equipment, tanks employed, the composition of the gas stream or energy source, etc. Such parameters may be readily selected by one of skill in the art in view of the teachings of this invention and are not a limitation of the invention.

In certain embodiments, the cyanobacteria are genetically modified to express one or more foreign genes encoding one or more enzymes that provide for transport of the products of photosynthesis from within the cell to the external culture media without significantly impairing the growth of the cyanobacteria. In addition, the genetically modified cyanobacteria also provide for secretion of the photosynthesis products without requiring the need for lysis of the cyanobacteria. By "foreign gene" is meant that the gene is not naturally found in the genome of the host organism, e.g., the cyanobacteria genome. The terms "products of photosynthesis" and "photosynthesis products" are used interchangeable and are used to mean the carbon-based compounds that are generated by the cyanobacteria as a result of the photosynthetic fixation of $CO_2$.

In some embodiments, the cyanobacteria are genetically modified to express one or more foreign genes that encoding one or more enzyme that facilitate active transport of the products of photosynthesis from within the cyanobacteria to the culture media. In one embodiment, an expression vector encoding a glucose transporter, such as the Glut-1 transporter (e.g., GenBank Accession No. S77924) can be introduced in the cyanobacteria in order to facilitate active secretion of glucose form within the cyanobacteria to the culture media. In another embodiment, a first expression vector encoding a fructose-6-phosphate isomerase can be introduced in the cyanobacteria in order to facilitate conversion of D-fructose 6-phosphate to D-glucose-6-phosphate. In such embodiments, a second expression vector is also introduced that encodes glucose-6-phosphatase (e.g., GenBank Accession Nos. AAA16222, AAD19898, O43826) that facilitates the conversion of D-glucose 6-phosphate and $H_2O$ to D-glucose and phosphate, and active secretion of the glucose form within the cyanobacteria to the culture media.

In other embodiments, the cyanobacteria are genetically modified to express one or more foreign genes that encode one or more enzymes that facilitate passive transport of the products of photosynthesis from within the cyanobacteria to the culture media. In some embodiments, the cyanobacteria are genetically modified to express foreign enzymes that facilitate further modification of the products of photosynthesis to other compounds that can then passively diffuse across the outer membrane of the cyanobacteria to the culture media.

For example, in one embodiment, a first expression vector encoding a pyruvate decarboxylase (also known as α-carboxylase; pyruvic decarboxylase; α-ketoacid carboxylase) (e.g., GenBank Accession Nos. AAB82395, CAA28380, CAA33709) (IUBMB Enzyme Nomenclature EC4.1.1.1), can be introduced in the cyanobacteria in order to facilitate conversion of a portion of pyruvate formed in photosynthesis to an aldehyde. In addition, a second expression vector is also introduced in the cyanobacteria that encodes an aldehyde dehydrogenase (also known as CoA-independent aldehyde dehydrogenase; m-methylbenzaldehyde dehydrogenase; NAD-aldehyde-dehydrogenase; NAD-dependent 4-hydroxynonenal dehydrogenase; NAD-dependent aldehyde dehydrogenase; NAD-linked aldehyde dehydrogenase; propionaldehyde dehydrogenase; aldehyde dehydrogenase (NAD)) (e.g., GenBank Accession Nos. AAA23428, AAC74382, BAA14869) (IUBMB Enzyme Nomenclature EC1.2.1.3), that facilitates conversion of the aldehyde from the reaction mediated by the pyruvate decarboxylase to an acid, such as acetic acid, which will passively diffuse through the cyanobacterial cell wall and into to external culture media.

In another embodiment, a first expression vector encoding a pyruvate dehydrogenase (also known as pyruvate dehydrogenase (NADP)) (e.g., GenBank Accession Nos. AAA34572, AAA34847, AAB64705) (IUBMB Enzyme Nomenclature EC1.2.1.51), and a second expression vector that encodes an acetyl-CoA kinase can be introduced in the cyanobacteria. In some embodiments, both foreign genes may be placed on a single expression vector. The pyruvate dehydrogenase and the acetyl-CoA kinase facilitate the conversion of a portion of pyruvate formed in photosynthesis to acetate, which will passively diffuse through the cyanobacterial cell wall and into to external culture media.

Microbial expression systems and expression vectors containing regulatory sequences that direct high level expression of foreign proteins are well known to those skilled in the art. Any of these could be used to construct vectors for expression of the genes in cyanobacteria. These vectors could then be introduced into the cyanobacteria via transformation to allow for expression of high level of the foreign enzymes.

Vectors or cassettes useful for the transformation of suitable microbial host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

There are two kinds of exemplary vectors for use in cyanobacteria, such as *Synechocystis*: self-replicating plasmids and chromosome integration plasmids. The self-replicating plasmids have the advantage of having multiple copies of coding regions of interest, and therefore the expression level can be very high. Chromosome integration plasmids are integrated into the genome by recombination. They have the advantage of being stable, but they may suffer from a lower level of expression. A specific embodiment of the present invention provides that the genetic construct resides on a plasmid in the transformed cyanobacterium. Alternatively, the genetic construct may be chromosomally integrated in the cyanobacterium genome.

Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Two sets of high level expression (i.e., strong) promoters from cyanobacteria *Synechocystis* sp. PCC6803 have been identified and can be used for expression of the foreign genes according to the present invention. For promoters in the *synechococcus* systems, promoters, such as RUBISCO promoters may be used. For example, in the *synechocystis* system, the native promoters for the glucose transporter will be attached to the foreign gene, such as Glut 1, and the native promoter and its native transporter in the glucose transporter will be deleted from the *synechocystis* bacteria.

Methanogenic Bacteria

Microbial methane formation, or methanogenesis, is a strictly anaerobic process carried out by a metabolically unique group of organisms in the kingdom of Archaea, known as methanogens. Exemplary suitable methanogens include those found in James G. Ferry, Methanogenesis (1993) (Chapman and Hall, New York, N.Y.). Representative examples include Methanosarcina and Methanothrix. Because methanogens are able to survive a variety of temperature ranges, these archaea are widely distributed in strictly anaerobic environments including the digestive tract of many animals (e.g., humans, termites, and the rumen compartment of ruminant animals), landfills, stagnant ponds, anaerobic digesters and rice paddies.

The selection of nutrients and other conditions for fermentation may be readily made by one of skill in the art with resort to existing knowledge, and depend on a variety of factors, such as the microorganism used, the size and type of the equipment, tanks and columns employed, the composition of the gas stream or energy source, etc. Such parameters may be readily selected by one of skill in the art in view of the teachings of this invention and are not a limitation of the invention.

Methods

As noted above, the present invention provides a two-step method for generating methane using biological organisms. In particular, the first-step includes using photosynthetic organisms to convert carbon dioxide to photosynthetic products. The second-step the photosynthetic products are used as nutrients for methanogenic bacteria that convert the photosynthetic products to methane. The photosynthesis is carried out in a first reaction chamber and the products of the photosynthesis, e.g., glucose and acetic acid, are collected and diverted to a second chamber for carrying out the methanogenesis. The product of the methanogenesis, methane gas, is subsequently collected and diverted to third chamber for storage.

Accordingly, the metabolic and methane production properties of the organisms described above indicate the design of an integrated system in which the photosynthesis and methanogenesis are employed in tandem to harvest radiant energy of the sun and to convert this solar energy into fuel in the form of methane. Such an exemplary integrated system would provide for a high yield, sustainable and viable methane gas production process using $CO_2$ as the carbon source.

Figure 2:
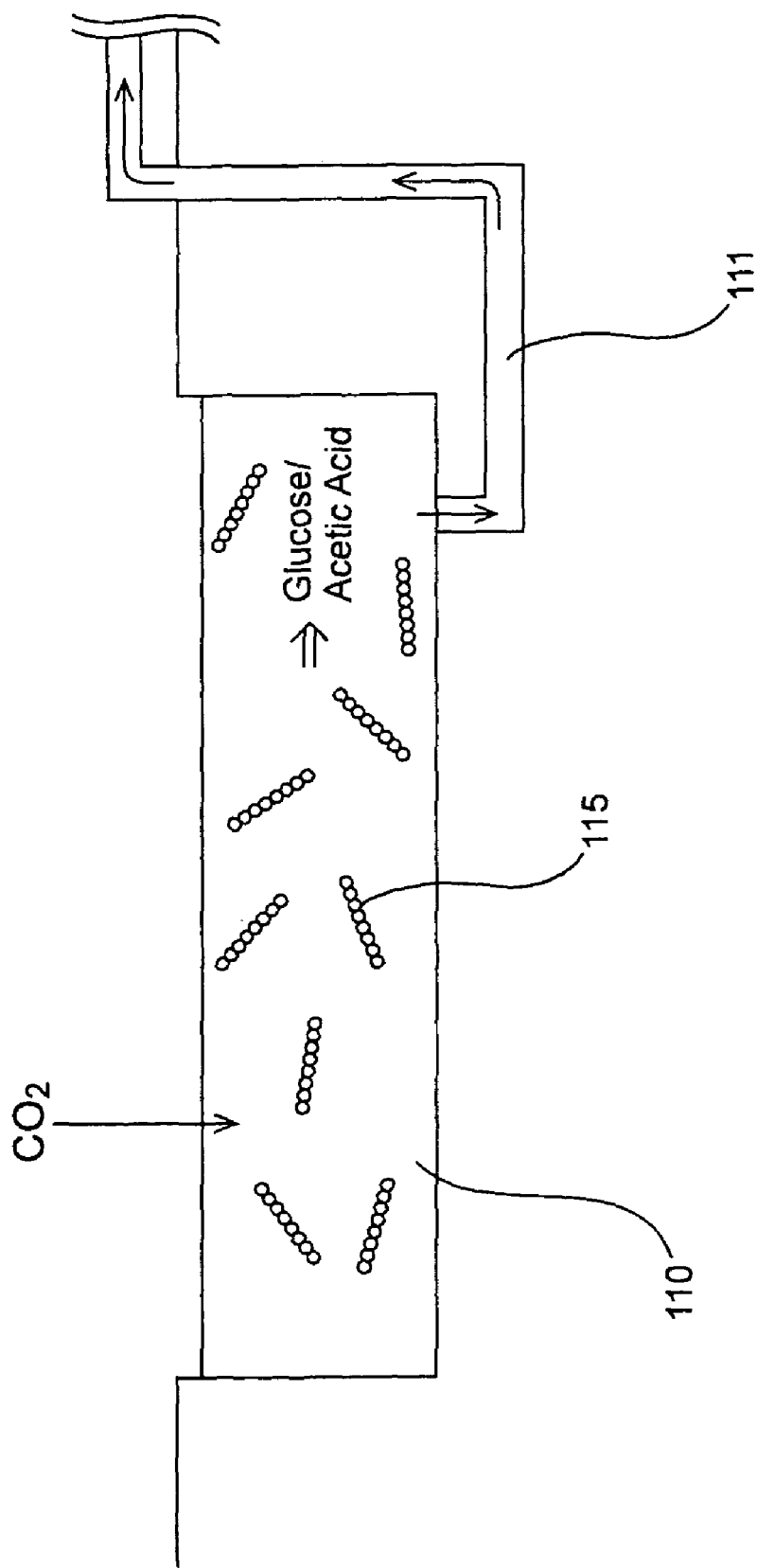
FIG. 2 is a close-up schematic view of the exemplary first culture vessel (110) for photosynthetic bacteria (115). The first culture vessel (110) allows for photosynthetic conversion of $CO_2$ from the atmosphere to photosynthesis products, such as glucose or acetic acid, by the photosynthetic bacteria (115)."
Figure 3:
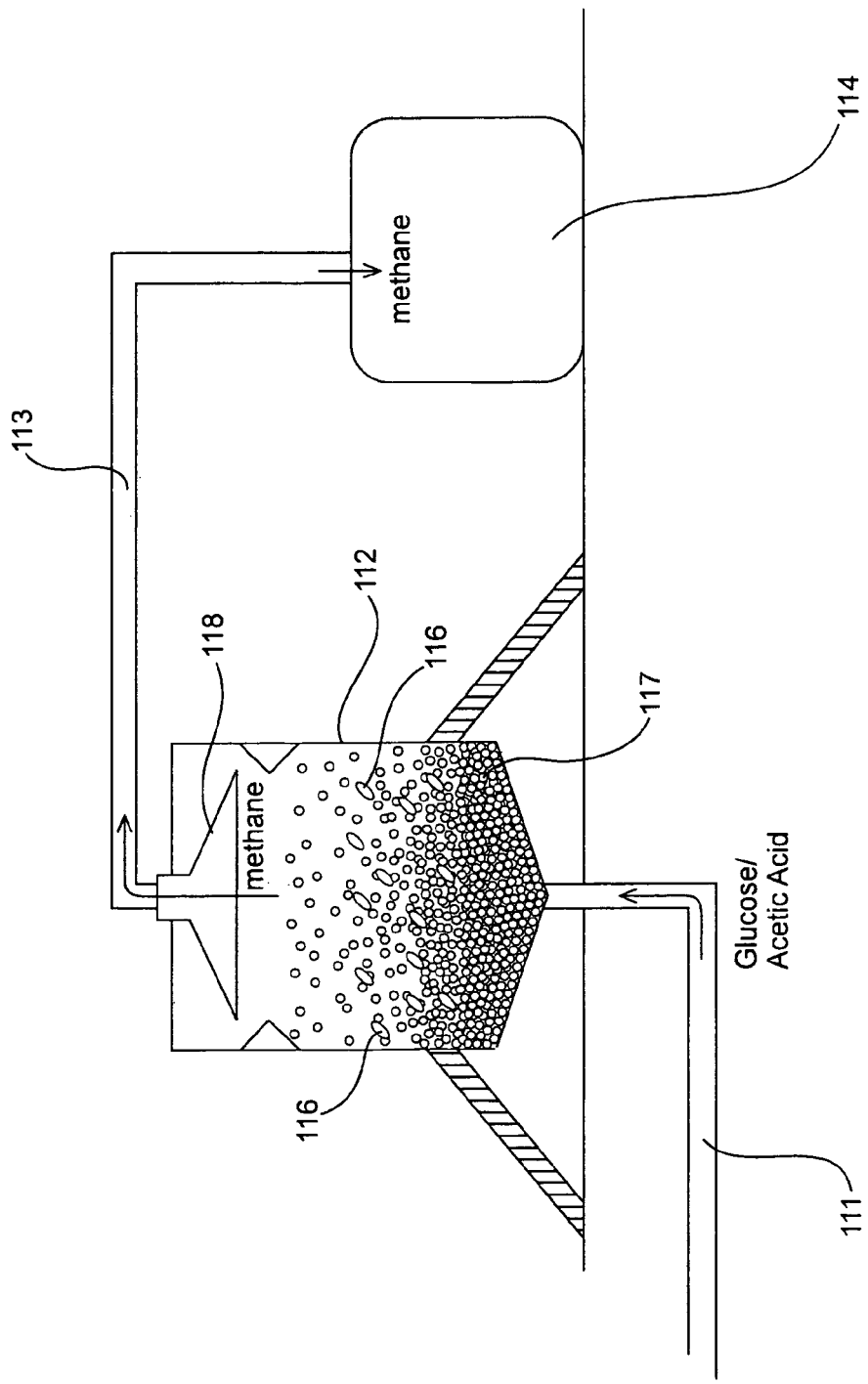
FIG. 3 is a close-up schematic view of the exemplary second culture vessel (112) for the methanogenic bacteria (116). The second culture vessel (112) allows for conversion of $CO_2$ the photosynthesis products, such as glucose or acetic acid, to methane by the methanogenic bacteria (116). The methane is collected and diverted to a storage container (114).

Referring to the drawing figures in general, and to FIGS. 1-3 specifically, a non-limiting example of a system (100) for producing methane from a two-step process is shown in schematic form in accordance with carrying out the methods of the present invention. The representative first culture vessel (110) is a long shallow vessel that maximizes photosynthesis in bacteria, such as cyanobacteria, that diffuse photosynthesis products. The photosynthetic products are transferred via a conduit to the send culture vessel (112) and serve as nutrients for the methanogenic bacteria present in the second culture vessel. The second culture vessel may contain more than one microorganism as is typical for bioreactors in sewage disposal plants so that different photosynthesis products can all be converted to proper nutrients for methanobacteria. In the process of translocating the nutrients from the first culture vessel (110) to the second culture vessel (112), cyanobacteria that may be translocated will be diverted and returned to the first culture vessel (110). The methane gas liberated in the first culture vessel (112) will collected and cleaned of contaminating gases, such as $CO_2$, $N_2$, and $H_2O$.

As will be readily appreciated by one skilled in the art, components of the system (100) (e.g., the first vessel (110), the second vessel (112), and the storage vessel (114) can be installed such that a portion of one or more of the vessels is placed underground or above ground. For example, the first vessel (110) may be installed as an above-ground pool with a transparent cover as long as it has an open top-surface in order to expose the contents of the vessel to light and atmospheric $CO_2$. Alternatively, the first vessel (110) may also be installed in the ground as a pool so long as the vessel has an open top-surface in order to expose the contents of the vessel to light and atmospheric $CO_2$.

Moreover, it will also be appreciated by one of skill in the art that while the invention is shown and described with respect to the exemplary embodiment represented in the figures, other changes in form and details may be made therein without departing from the spirit and scope of the invention. For example, the size and the depth of the first vessel may be adjusted in order to maximize the exposure of the cyanobacteria to the maximum amount of light. In addition, the size of the vessel may also be adjusted in order to maximize the exposure of the cyanobacteria to maximum amount of atmospheric $CO_2$.

Prior to implementation of the method of the invention, the first vessel (110) is inoculated with a predetermined amount of the first mixture of cyanobacteria as a "starter" culture. The quantity of starter culture used is a function of the intended steady state mixed concentration of the cyanobacteria in the vessel, the size of the vessel and the maximum food-to-microorganism ratio (F/M). Generally, the starter culture may be obtained from a lyophilized stock, or from another growth reactor tank using the same organisms and conditions.

In order to mediate photosynthesis, the cyanobacteria will require light. Light, generally in the form of natural sunlight or suitable artificial light, is irradiated onto the first vessel (110) containing the mixture in order to promote photosynthesis by the cyanobacteria (115), and to promote growth of the organisms. If artificial light is used, it is generally preferable to utilize a broad spectrum of light that is similar to sunlight, for example, fluorescent lights such as CORALIFE 50/50 Actinic/Daylight type, CORALIFE™ Trichromatic Super Daylight type, and the like, generating light in the range from 400-1000 nm. The artificial lighting is preferably controlled by a photoelectric switch or timer. Additionally, conduits used in the apparatus of the invention may be made of a clear or transparent material to enhance exposure to light.

Under certain conditions in which the level of natural, ambient light is low, (e.g., high latitudes or during winter months), addition of a supplemental photobioreactor to the present invention can increase the amount of light made available to the cyanobacteria, and result in improved photosynthesis. The supplemental photobioreactors implemented in such an embodiment provide additional light to the growing cyanobacteria to enhance and optimize the growth rate of the organisms. Addition of the photobioreactors therefore results in an increased overall efficiency of the process of the invention and can provide additional light to the organisms during times at which ambient light levels are low (e.g., winter months). Examples of useful photobioreactors according to the method of the invention include coiled tubular photobioreactors of the type described and illustrated in U.S. Pat. No. 5,137,828, herein incorporated by reference in its entirety, and available commercially under the tradename BIOCOIL™ and are available from Biotechna Environmental International, LTD.

Briefly, such photobioreactors typically comprise an upstanding core structure, and a substantially transparent tube wound on the core structure, or tubes wound in parallel on a manifold such that the exterior of the tubes are exposed to light. The upstanding core structure preferably includes a reflective coating, such as white paint, aluminum foil, small glass balls, and the like, interposed between the core structure and the transparent tubing. This reflective coating enhances light penetration into the transparent tubing in the region where the transparent tubing and the core structure make contact and thereby increases the amount of available light. Additional photobioreactors that may be used according to the process of the present invention are described in British Patent Application No. 9719965.7, and in U.S. Pat. Nos. 4,868,123; 4,952,511; 5,162,051; and 5,447,629.

In some embodiments, the first vessel (110) may further include an aeration device. The term "aeration device" refers to a device that introduces $CO_2$ into a reactor. Aeration devices include mechanical aerators or compressed air. In some embodiments, the aeration device is a mechanical aeration device that includes a mechanical arm (e.g., a paddle stirrer, or other mixing means known in the art) that created movement within the device in order to provide exposure to atmospheric $CO_2$ for the cyanobacteria. In some embodiments, a recirculating pump may be used to mix and aerate the solution. If a recirculating pump is used, the return lines may be made from a clear or transparent material so that the contents of the return line are exposed to light as described above.

The rate of recirculation, in addition to the direct exposure to light in the growth reactor tank, is preferably controlled to develop the proper light-to-dark ratio for optimum growth of the photosynthetic organisms. During periods of daylight hours and/or exposure to artificial light, the present invention is typically operated with flow rates that maintain a light to dark ratio of approximately 1:600. During summer operations when natural light is at high intensity, this dark to light ratio is sufficient to maintain optimum growth. During low light periods the optimum light to dark ratio should be increased wherein light to dark volume may be as great as 1:1 or higher. As will be apparent to those skilled in the art, the conditions sufficient to achieve optimum growth will vary depending upon location, climate, and other environmental factors, such as the diurnal cycle, light intensity and time of exposure to light. Accordingly, adjustments may be required take such factors into account.

The tank contents are preferably mixed gently to avoid lysing or otherwise killing the proliferating cells. Continuous mixing of the components in the first stage growth reactor tank 6 serves several important functions, including promoting uniform contact between all the proliferating cells, soluble and colloidal waste constituents, and light, and maintaining a uniform temperature throughout the mixture. Useful temperatures of the first stage growth reactor tank 6 should generally be maintained in the range of from 28 to 40° C. In certain climates, ambient air temperature is sufficient to maintain the temperature within this range. Alternatively, the temperature of the first stage growth reactor tank 6 may be controlled using conventional heating apparatus, such as fossil fuel or solar heaters with suitable recirculating heat exchangers and associated controls. In all applications of the invention, however, the processing conditions are preferably closely controlled (e.g., temperature maintained within +/−2° C.).

Alternatively, production of photosynthesis products from $CO_2$ fixation mediated by the cyanobacteria may also be accomplished with a continuous culture. Continuous cultures are an open system where a defined culture media is added continuously to a vessel and an equal amount of conditioned media is removed simultaneously for processing. Continuous cultures generally maintain the cells at a constant high liquid phase density where cells are primarily in log phase growth.

As noted above, as the photosynthesis products are generated and transported into the external culture media, the photosynthesis products are collected and diverted to a second culture vessel (114) comprising the methanogenic bacteria, which facilitates methanogenesis. As such, in representative embodiments, the first vessel (110) is in fluid communication with a first transport conduit (111), and the first transport conduit (111) is in fluid communication with the second culture vessel (112). Therefore, in representative embodiments, the system provides for movement of material (e.g., photosynthesis products) via conduits or connecting means from one vessel to another (e.g., aerobic culture bed, anaerobic reactor or fermenting chamber, filtration devices, and storage containers). Those of skill will recognize that a vessel comprises inlets and outlets to allow material to pass to or through a vessel during the operation of the claimed invention.

The term "conduit" refers to a passageway for transfer of liquid or gas from one vessel to another. Exemplary conduits are tubing or pipe, although a conduit is not limited to a single tubing or pipe. Conduit also encompasses a direct connection from one vessel to another. Pumps and valves can be included in a conduit to facilitate transfer of a liquid or gas. In addition to tubing or pipe conduits can include other elements of the invention, e.g., an anaerobic or aerobic reactor, a sludge holding member and/or a sludge dewatering device, a filtration device, or a desalinization device. Connecting means is used interchangeably with conduit.

In certain embodiments, the collecting and diverting of the photosynthesis products present in the external culture media is carried out by use of a pump means. As will be appreciated by one of skill in the art, the pump means may be situated at any point between the first vessel (110), the first conduit (111), and the second vessel (112). In some embodiments, the pump means will be situation at a point in between the first vessel (110) and the inlet to the first conduit (111).

Prior to implementation of the method of the invention, the second vessel (112) is inoculated with a predetermined amount of the first mixture of methanogenic bacteria as a "starter" culture. The quantity of starter culture used is a function of the intended steady state mixed concentration of the methanogenic bacteria in the vessel, the size of the vessel and the maximum food-to-microorganism ratio (F/M). Generally, the starter culture may be obtained from a lyophilized stock, or from another growth reactor tank using the same organisms and conditions.

The second vessel (112) will generally be an enclosed container suitable for establishing an anaerobic environment for the methanogenic bacteria. As will be readily appreciated by one skilled in the art, components of the second vessel (112) can be installed such that a portion of one or more of the vessels, or the entire vessel is placed underground or above ground as long as the vessel is enclosed (e.g., prevents exposure of the contents of the vessel to the atmosphere). In certain embodiments, the second vessel (112) can be designed similar to an up-flow anaerobic sludge bed (USAB) reactor that includes a sludge bed and sludge blanket (117) as exemplified in FIG. 3. The USAB reactor typically includes a polymer suitable for a species of methanobacteria to form a biofilm. As the $CH_4$ gas is formed it is collected in an outlet at the top of the vessel where it will be collected. If the nutrient that is provided for the methanogenic bacteria is glucose, the second reaction vessel may further include acetogenic bacteria to facilitate conversion of the glucose to acetic acid.

Fluid levels in the reaction vessel may be monitored with a fluid level detector and controlled with a fluid level controller that either increases or decreases the flow of media containing the photosynthesis products from the first conduit (111) into reaction vessel.

In some embodiments, it may be desirable to operate the second vessel (112) at higher pressures in order to produce higher quality, i.e., purer, methane. Generally, the higher the digester pressure, the higher the purity or BTU rating of methane produced by the second reaction vessel (112). Under anaerobic, the second vessel (112) will generally not require pressurization by external means as gas formation in the digester tends to pressurize the vessel sufficiently. However, the reaction vessel can be pressurized with a pressurizer. The pressurizer can be a compressed gas cylinder, pump, or other such equipment, that forces an inert gas, or reaction effluent into the reaction vessel to increase the pressure of the reaction vessel to above about 10 psi. In such embodiments, the second vessel (112) will further comprise one or more pressure relief valves, vents or exhaust valves to reduce pressure within the reaction vessel. In such embodiments, the second vessel (112) will also preferably comprise a pressure controller capable of controlling pressure within reaction vessel and/or a pressure monitor capable of monitoring pressure within the reaction vessel. The second vessel (112) can also comprise one or more pressure gauges that indicate the pressure within the system.

Temperature can also affect the productivity of the anaerobic conditions within the second vessel (112). Therefore, in some embodiments, it is desirable to elevate the temperature within the reaction vessel (112) in order to increase the productivity, e.g. faster or more efficient gas production. As will be apparent to one skilled in the art, different microbes have different optimal temperatures. Therefore the level of temperature will be dependent on several factors including, but not limited to, the size of the vessel, the ambient temperature of the vessel, the particular methanogenic bacteria used, and the like. The temperature of the reaction solution can be controlled with a temperature controller that heats and/or cools the reaction solution. The temperature controller can be a heater, heat exchanger, jacket surrounding the reaction vessel, coil within the reaction vessel or other such equipment used for controlling the temperature of fluids within reactors. The temperature of the reaction vessel will generally be monitored with a temperature monitor, such as a thermocouple or other equipment known to those of ordinary skill in the art. A heating or cooling jacket surrounding the reaction vessel is alternatively used to control the temperature of the reaction vessel contents.

Methane gas generated in the second vessel (112) may be captured or collected using a variety of piping arrangements in accordance with the present invention. In FIG. 3, the second vessel (112) is connected to gas/solid separator (118) that facilities separation of the methane gas from the solid material in the second vessel. The gas/solid separator (118) is then connected to a riser pipe or second conduit (113) which connects to a storage tank (114). In this exemplary arrangement, methane can be collected in the storage container (114) as it is produced in the second reaction vessel (112). In some embodiments, the conduit (113) may require special reinforcements or materials suitable for withstanding pressures associated the subject system. These structural reinforcements and materials are generally known and therefore will not be described in detail herein. In such exemplary system, methane may be further piped from the storage tank (114) to smaller transportation tanks used for transporting the methane to remote locations.

The methane produced by the subject method may also be cleaned or purified by a scrubber to remove moisture, vapor, droplets, suspended solids or other such contaminants. The scrubber can comprise one or more of a filter, desiccant, zeolite, activated carbon, fiber, countercurrent wash solution, mixer, homogenizer, or other such components typically used in association with or comprised within gas scrubbers. Such components are well known to those of ordinary skill in the art of gas processing.

While the invention has been particularly shown and described with respect to the illustrated embodiments thereof, it will be understood by those skilled in the art that the foregoing and other changes in form and details may be made therein without departing from the spirit and scope of the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Methods and Materials

The following methods and materials are used in the examples below.

Pathway Engineering in *Synechococcus* Using Shuttle Vector System

Desired gene(s) from different pathways which can lead to acetate production were incorporated into modified shuttle vector systems derived from shuttle vector pCB4. These vectors can replicate in either *E. coli* or *Synechococcus*.

Introduction of T7 or T7 lac Promoter

To control the protein expression level of the introduced genes, T7 or T7lac promoter was cloned into the vector. The T7 promoter was cloned using the following oligonucleotides. 5'-AATTCCGATCCCGCGAAATTAATACGACTC-ACTATAGGGAGACCACAACGGTTTCCCTTCAGAAA-TAATTTTGTTTAACTTTAAGAAGGAGATATAG-3' (SEQ ID NO:01) (containing EcoR I and BamH I restriction sites) and 5'-GATCCTATATCTCCTTCTTAAAGTTAAACAAA-ATTATTTCTGAAGGGAAACCGTTGTGGTCT CCCTAT-AGTGAGTCGTATTAATTTCGCGGGATCGG-3' (SEQ ID NO:02). The oligonucleotides were designed by using the T7 promoter sequence from pET-3a. The oligonucleotides were then phosphorylated and annealed together to synthesize a T7 promoter cassette with EcoR I and BamH I on either end. Then the resulting cassette was ligated into pUCl 8 vector pretreated with EcoR I and BamH I restriction enzyme. The resulting plasmid was named pjXSOO (pUC-T7P). T7lac promoter was introduced using a similar strategy.

Introduction of Terminator Region

To provide for termination the gene transcription, a T7 terminator was introduced. A T7 terminator was constructed using the following oligonucleotides: 5'-AGCTTCTAGCAT-AACCCCTTGGGGCCTCTAAACGGGTCTTGAGGGGT-TTTTTGATATCA-3' (SEQ ID NO:03) and 5'-TATGATAT-CAAAAAACCCCTCAAGACCCGTTTAGAGGCCCCA-AGGGGTTATGCTAGA-3' (SEQ ID NO:04) (containing EcoR I and Nde I restriction site overhangs) were designed. The oligonucleotides were then phosphorylated and annealed together to synthesize a T7 terminator cassette. The resulting cassette was then ligated into pUCIS vector pretreated with Hind III/Nde I. The resulting plasmid was named pJX301_pUC-T7tt. The T7 terminator containing fragment was subsequently subcloned into pJX300 to obtain plasmid pJX302_pUC-T7P+T7tt which contained a T7 promoter region (EcoR I-BamH I), a T7 terminator (Hind III-Nde I), and a multiple cloning site (MCS) in between the promoter and terminator regions.

Introduction of Cyanobacteria Specific Promoter rbcL

The promoter region of the rbcL gene (RUBISCO Large subunit) of *Synechococcus* sp. PCC7942 strain was cloned and used to express the gene(s) in the cyanobacteria. Different restriction site overhangs were added to the promoter region to facilitate subsequent insertion of a gene of interest. Below is a brief description of cloning using Bam HI/Sal I overhang. The forward primer 5'-CGCGGATCCGCGGCTGAAA-GTTTCGGACTCAGTAG-3' (SEQ ID NO:05) (containing a Bam HI site) and the reverse primer 5'-GGCATGTC-GACTCTCCCTAGAGATATGTCAG-3' (SEQ ID NO:06) (containing a Sal I site) were used to clone the rbcL promoter region from genomic DNA of *Synechococcus* sp. PCC7942. The PCR products were then treated with BamH I and Sal I and ligated into pJX302 plasmid.

Introduction of Gene(s) of Interest

To increase the acetate production level, the gene(s) from two different acetic acid production pathways were introduced into cyanobacteria. One pathway involves PDC (pyruvate decarboxylase) and AldDH (aldehyde dehydrogenase) genes; the other pathway involves POX (pyruvate oxidase) and ackA (acetate kinase) genes. AldDH and ackA are present in the *Synechococcus* genome. To increase the acetate yield, PDC alone, PDC and AldDH genes, POX alone, or POX and ackA were introduced into cyanobacteria on expression vectors. The *Zymomonas mobilis* PDC gene was amplified from pLOI295 (Ingram et al., Appl Environ Microbiol. 53(10): 2420-2425 (1987)) using the following primers: forward primer 5'-GGAGGTCGACATGAGTTATACTGTCGG-TACC-3' (SEQ ID NO:07) (containing a Sal I restriction site) and reverse primer 5'-CGCTGCAGTTACTAGAGGAGCT-TGTTAACAGGC-3' (SEQ ID NO:08) (containing a Pst I restriction site and one extra stop codon). The resulting 1.7 kb fragment was restriction digested and ligated to give plasmid pJX346 (pUC-PT7rb+PDC+T7tt), which is a pUC18 derivative and contains T7 promoter, rbcL promoter, PDC gene, and T7 terminator. Finally, the 2.2 kb EcoR I-Nde I fragment of pJX346 was ligated into a pCB4 shuttle vector. The resulting plasmid was named pJX348 (pCB-PT7rb+PDC+T7tt).

The AldDH gene was introduced upstream of the PDC gene under the same promoter. One addition ribosome binding site (RJBS) was introduced adjacent to its 5' end. The AldDH gene was amplified from *Synechococcus* genomic DNA using the following primers: forward primer 5'-GAG-GCATGCGGAGGTGCTGCCATGACTGCTGTCGTTCT-CC-3' (SEQ ID NO:09) (containing a RBS and Sph I restriction site) and reverse primer 5'-GCTGCATGCACTA-GAGCTTGCGGAAGAGG-3' (SEQ ID NO:10). The resulting PCR fragment was restriction digested by Sph I and ligated into pJX348.

POX gene was then cloned from *Lactobacillus plantarum* WCFS1. The forward primer 5'-CGCTCTAGAATGGTTAT-GAAACAAACAAAAC-3' (SEQ ID NO:11) (containing a Xba I site) and the reverse primer 5'-GCGCTGCAGCTAT-TAAAACCCACCCTGTCCAATTTG-3' (SEQ ID NO:12) (containing a Pst I site and one extra STOP codon) were designed based in the POX5 sequence of *Lactobacillus plantarum* WCFS 1. By following a similar strategy above, plasmid pJX371 (PT7lacRB+POX+T7tt), which contains T7lac promoter, rbcL promoter, POX gene, T7 terminator, was constructed and used to transform *Synechococcus* strain.

AckA gene was further introduced downstream of POX gene. The forward primer 5'-GAGGCATGCGGAGGAGC-CTGTTCAGATGCTGGATAGCAGCGATCG-3' (SEQ ID NO:13) (containing a RBS and a Sph I restriction site) and the reverse primer 5'-GCTGCATGCCTATCAATTGAAA-GACTGTGGGGATCG-3' (SEQ ID NO:14) (containing a Sph I restriction site) were designed based on the ackA sequence from *Synechococcus*. The resulting plasmid pJX373 (pCB-PT7lacRB+POX5+ackA+T7tt) (FIG. 5), which contains T7lac promoter, rbcL promoter, POX gene, ackA gene, and T7 terminator was constructed and used to transform *Synechococcus* strains.

Example 1

Generation of Genetically Modified Cyanobacteria

The unicellular freshwater cyanobacterium *Synechococcus elongates* PCC7942 (previously known as *Anacystis nidulans* R2) and plasmid-containing derivatives were used in this study. *Zymomonas Mobilis* pyruvate decarboxylase gene (zmPDC) was cloned from plasmid pLOI295 (Ingram et al., Appl Environ Microbiol. 53(10): 2420-2425 (1987)). Pyruvate oxidase (POX) gene was cloned from the genomic DNA library of *Lactobacillus plantarum* (ATCC). The aldehyde dehydrogenase (aldDH) and acetate kinase (ackA) genes were cloned from *Synechococcus elongates* PCC 7942 genome directly.

Cells were grown in 200 BG-11 medium in 500 mL Erlenmeyer flask capped with BUGSTOPPER™ 10 (Whatman Inc., Clifton, N.J.). The cultures were agitated constantly at the speed of ~100 rpm on a stirrer plate. The cultures were grown at either room temperature or at 30° C. under white fluorescence light (1000-1200 lux). The growth was monitored by measuring the optical density at 730 nm.

For BG11 agar plate preparation, 15 g DIFCO™ Bacto-agar, 10 mL 1MTES/NaOH buffer (pH-8.2), 3 g Na-thiosulfate were added per 1 L BG-11 media. If need, sterile-filtered solution were added after the medium was autoclaved and cooled down to 55° C. (5 mN glucose, 15 mM acetate, kanamycin, chloramphenicol, streptomycin or ampicillin). The plates were illuminated under the same condition as liquid culture.

Transformation of *Synechococcus elongates* PCC 7942 was carried out as following: wild type or mutant strain was grown to log phase ($OD_{730}$~0.5). Then 10 ml culture was collected and cells were spin down at 4,000 g for 5 min. The cell pellet was washed twice by resuspending the cell pellet in 10 mL fresh BG11 buffer and then spun down in a centrifuge. Then the cells were then resuspended in 1 mL BG11 buffer. To transform the cells, 1-10 ug plasmid DNA was added to the solution. The mixture was incubated at 30° C. under illumination for 8 hours. The cells were plates on BG11 agar plates with proper antibiotics. The plates were then incubated at 30° C. under illumination.

The plasmid vectors to introduce different pathways were modified based on the shuttle vector pCB4. In this vector, a polylinker site was incorporated into the position of the unique Bam HI restriction site. Then the promoter region of rebels (RubisCO large subunit) was cloned to facilitate the expression of different genes in the cyanobacteria. To test the expression of the same genes in *E. coli*, T7 promoter was introduce upstream of rbcLS promoter. This allows for testing of protein expression in *E. coli*. Furthermore, T7 terminator was introduced into the end of polylinker region. The resulting plasmid vector (pDEK-SE1) will be used for the pathway engineering.

Figure 4:
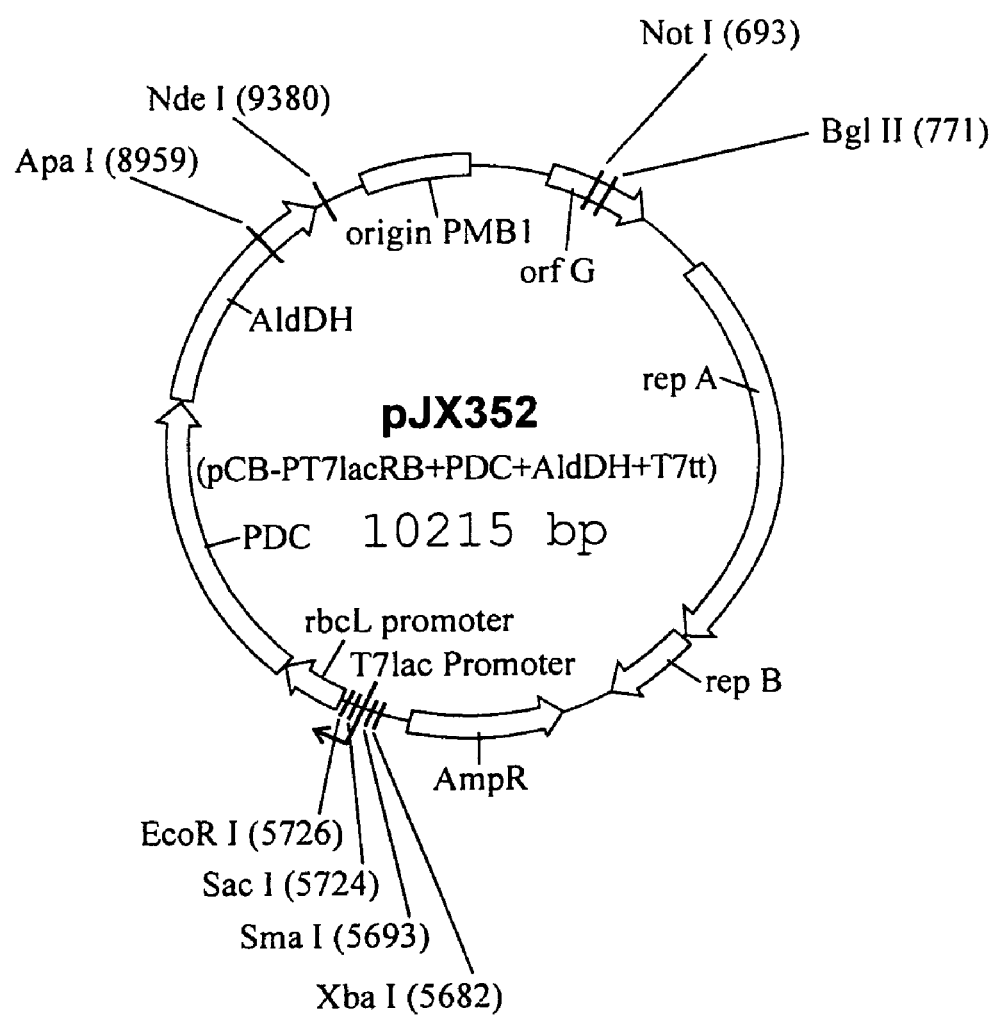
FIG. 4 is a schematic of the pJX352 plasmid used to express genes in cyanobacteria. The vector is a pCB4 shuttle vector derivative that includes an ampicillin resistance gene (AmpR), T7lac promoter, rbcl promoter (Rubisco large unit), pyruvate decarboxylase gene (PDC), and aldehyde dehydrogenase gene (AldDH).
Figure 5:
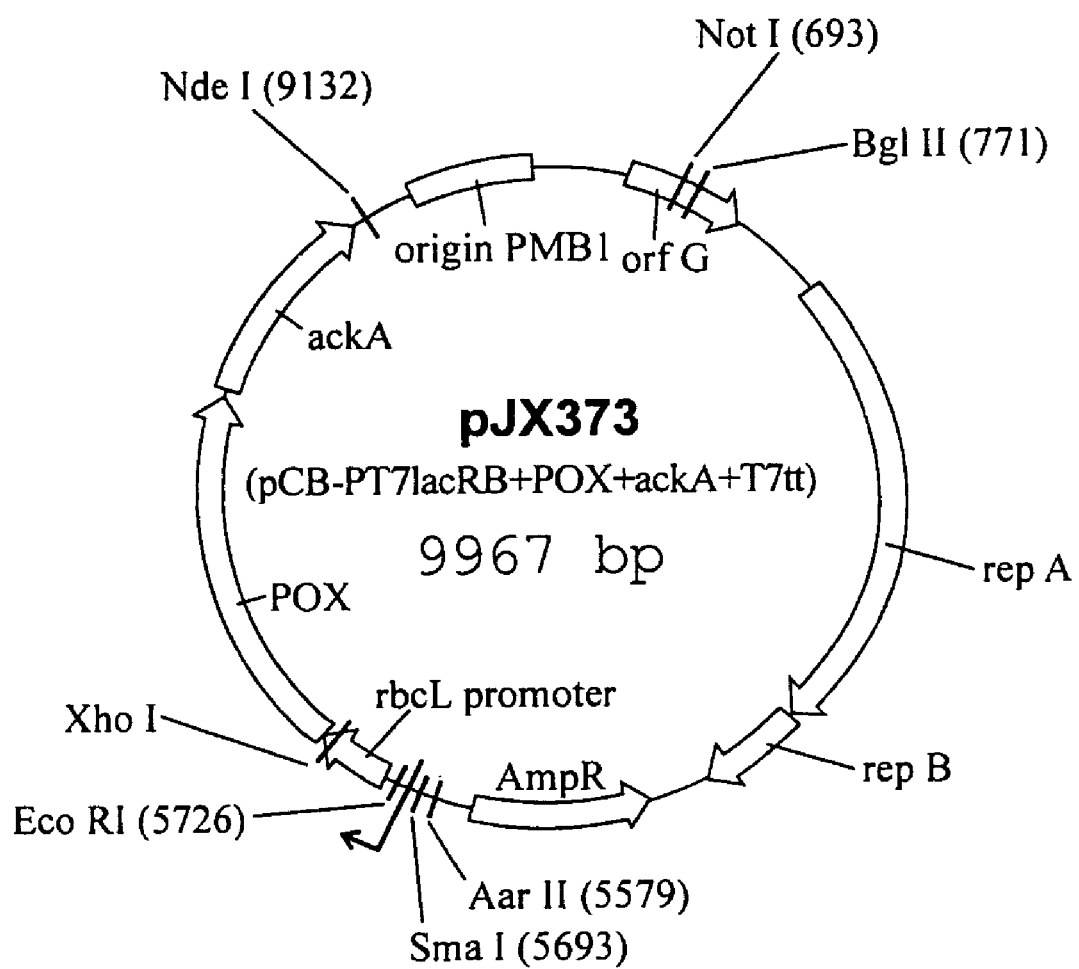
FIG. 5 is a schematic of the pJX373 plasmid used to express genes in cyanobacteria. The vector is a pCB4 shuttle vector derivative that includes an ampicillin resistance gene (AmpR), T7lac promoter, rbcl promoter (Rubisco large unit), pyruvate oxidase gene (POX), acetate kinase gene (ackA), and a T7 terminator sequence.

Currently, two pathways, which convert pyruvate to acetate, were introduced into pDEK-SE1. The genes involved in the first pathway are pyruvate decarboxylase and aldehyde dehydrogenase (pdc-aldDH). The other pathway contains pyruvate oxidase and acetate kinase (pox-ackA) pdc-aldDH or pox-ackA was put in the same transcript under the control rbcLS promoter cyanobacteria. For the region between the two genes, one ribosome binding site was introduced while no terminator sequence was present. The resulting plasmids were named pJX352 expressing pdc-aldDH (FIG. 4) and pJX373 expressing pox-ackA (FIG. 5).

Example 2

Production of Acetic Acid from Genetically Modified Cyanobacteria

To produce acetic acid, *Synechococcus* PCC7942 were first transformed with the pJX352 plasmid or the pJX373 plasmid and plated on BG11/carbenicillin and incubated at room temperature under illumination for several days until single colonies developed. Single colonies were then picked using a sterile P200 pipette tip and inoculated 4 ml of liquid BG11/carbenicillin growth medium in a glass tube. The culture was incubated with shaking at room temperate overnight under illumination. Prior to starting the large scale culture, the optical density at 730 nm of the 4 ml culture was measured when the culture reached a fairly green color. Once the optical density reached approximately 1.0 (stationary growth phase), 2 ml of the starter culture was transferred to a sterile 200 ml BG11/carbinicillin liquid growth medium in a 500 ml flask. The 200 ml culture was grown at room temperate while shaking and under illumination. Periodically, the optical density of the culture at 730 nm was monitored by removing a 1 ml sample and measuring the optical density in a cuvette.

Once the culture had reached an optical density of approximately 0.5 (e.g., log phase growth) and approximately 1.0 (e.g., stationary growth phase), 50 ml samples were removed and placed in 50 ml Tubes. The samples were centrifuged at 6 k rpm for 10 minutes. The supernatants were decanted into separate tubes and the pellets as well as the supernatants were saved. Acetic acid assays were then performed on the supernatants to determine the level of acetic acid production and secretion by the genetically modified cyanobacteria in the medium. The Megazyme Acetic Acid kit (Acetyl-CoA synthase) protocol was followed for measuring acetic acid. 2.1 ml of sample were used and at least one acetic acid standard was run with every assay (e.g., 50 µM or 100 µM acetic acid). The results of the acetic acid kit are provided in Table 1. The results show that the modified cyanobacteria are capable of efficiently producing and secreting acetic acid into the medium as compared to the controls.

medium was adjusted to 6.8 before autoclave. All medium was prepared in an atmosphere of oxygen free 80% $N_2$-20% $CO_2$. All media were dispensed into Hungate tubes or flasks closed with butyl rubber stoppers and aluminum seals. The solution was then treated in the standard protocol for anaerobic incubation, such as boiling and cooling under a stream of nitrogen to eliminate oxygen from the medium.

Trace Element Solution SL-6 included 0.1% $ZnSO_4.7H_2O$, 0.003% $MnCL_4H_2O$, 0.03% $H_3BO_3$, 0.2% $CoCl_2.6H_2O$, 0.001% $CuCl_2.2H_2O$, 0.002% $NiCl_2.6H_2O$, and 0.003% $Na_2MoO_4.6H_2O$. Wolf's Vitamin Solution included 0.0002% Biotin, 0.0002% Folic acid, 0.001 Pyridoxine HCl, 0.0005% Thiamine HCl, 0.0005% Riboflavin, 0.0005% Nicotinic acid, 0.0005% Calcium-D-(+)-pantothenate, 0.00001% Cyanocobalamine, 0.0005% p-aminobenzoic acid, and 0.0005% Thioctic acid. $NaHCO_3$ solution was prepared by dissolving 850 mg $NaHCO_3$ in 20 mL of water. The $Na_2S$/Cystein Reducing agent was prepared by mixing 3% Cysteine $HCl.H_2O$ and 3% $Na_2S.9H_2O$ together.

Cultures were inoculated with 6 mL media on different acetate concentrations (10 µM-10 mM) at 30° C. from media collected from the genetically modified cyanobacteria. The incubation mixture was grown under anaerobic conditions. The initial culture was done on 1 mM sodium acetate concentration. Three days after the inoculation of the cultures, methanogen cell growth on the acetate present in the media was evident by the turbidity of the medium and settlement at the bottom of the test tube.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language

TABLE 1

| Strain/Name | A0 | A1 | A2 | Delta | Acetic Acid Conc. (g/L) | Acetic Acid Conc. (µM) | OD |
|---|---|---|---|---|---|---|---|
| Blank | 0.0648 | 0.3048 | 0.3319 | | | | |
| 50 µM NaAc | 0.0758 | 0.3095 | 0.4781 | 0.2153 | 0.002775 | 46.21 | |
| 351 | 0.1317 | 0.3649 | 0.4462 | 0.0902 | 0.0011627 | 19.36 | 0.8200 |
| 352 | 0.1248 | 0.3571 | 0.4239 | 0.0673 | 0.00086753 | 14.45 | 0.7300 |
| 368 | 0.1567 | 0.3903 | 0.5033 | 0.1378 | 0.0017763 | 29.58 | 0.8900 |
| 371 | 0.1660 | 0.3993 | 0.5093 | 0.1333 | 0.0017183 | 28.61 | 0.8700 |
| 373 | 0.1633 | 0.4000 | 0.4991 | 0.1176 | 0.0015159 | 25.24 | 0.8600 |
| pCB4 | 0.1400 | 0.3742 | 0.4614 | 0.0993 | 0.00128 | 21.32 | 0.7500 |

Example 3

Growth of Mentanobacterium on Acetic Acid Containing Medium from Genetically Modified Cyanobacteria Methanosarcina barkeri strain was obtained form the American Type Cell Culture (#29786). Methanosarcina medium was modified from ATCC media #1043 broth to include 0.0348% $K_2HPO_4$, 0.0227% $KH_2PO_4$, 0.05% $NH_4CL$, 0.25% $CaCl_2$, 0.00002% $FeSO_4.7H_2O$, 0.3% Trace Elements Solution SL-6, 1% Wolf's Vitamin Solution, 0.2% Yeast Extract, 0.2% Casitone, 0.225% NaCl, 0.0001% Resazurin, 2% $NaHCO_3$ solution, and 2% $Na_2S$/Cysteine reducing agent. All the ingredients were mixed except Wolf's Vitamin Solution and $Na_2S$/Cysteine solution and autoclaved at 121° C. for 15 minutes. Wolf's Vitamin Solution and $Na_2S$/Cysteine solution were subsequently added. The pH of the recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for production of methane, comprising:
culturing a photosynthetic cyanobacteria in a first vessel in the presence of carbon dioxide ($CO_2$) and visible light, wherein the culturing provides for photosynthetic fixation of $CO_2$ to produce photosynthesis products, and wherein the photosynthetic cyanobacteria comprises at least one expression cassette comprising at least one gene that encodes for pyruvate decarboxylase, pyruvate dehydrogenase, aldehyde dehydrogenase or acetyl-CoA kinase, wherein the at least one expression cassette provides for modification of the photosynthesis products to products that can passively diffuse out of the cell,
collecting and diverting the photosynthesis product in the absence of the photosynthetic cyanobacteria to a second vessel comprising methanogenic bacteria, and
culturing said methanogenic bacteria to produce methane.

2. The method of claim 1, wherein said photosynthesis product is glucose or acetic acid.

3. The method of claim 1, wherein the cyanobacteria further comprises at least one expression cassette comprising glucose transporter gene Glut-1 that provides for active transport of the photosynthesis products out of the cell.

4. The method of claim 1, wherein visible light source is natural light.

5. The method of claim 1, wherein a visible light source is artificial light.

6. The method of claim 1, wherein a $CO_2$ source is atmospheric $CO_2$.

7. The method of claim 1, wherein a $CO_2$ source is an artificial source.

8. The method of claim 1, wherein the cyanobacteria is a *Synechococcus* species of cyanobacteria or a *Synechocystis* species.

9. The method of claim 1, wherein the at least one expression cassette comprises a gene that encodes for pyruvate decarboxylase and a gene that encodes for aldehyde dehydrogenase.

10. The method of claim 1, wherein the at least one expression cassette comprises a gene that encodes for pyruvate dehydrogenase and a gene that encodes for acetyl-CoA kinase.

* * * * *